United States Patent
Zuo et al.

(10) Patent No.: US 11,517,461 B2
(45) Date of Patent: Dec. 6, 2022

(54) GASTRIC DIVERTER AND DIGESTIVE TRACT SUPPORT AND RELEASE METHOD THEREOF

(71) Applicant: HANGZHOU TANGJI MEDICAL TECHNOLOGY CO. LTD, Hangzhou (CN)

(72) Inventors: Yuxing Zuo, Hangzhou (CN); Yan Lu, Hangzhou (CN)

(73) Assignee: HANGZHOU TANGJI MEDICAL TECHNOLOGY CO. LTD, Zhejiang (CN)

( * ) Notice: Subject to any disclaimer, the term of this patent is extended or adjusted under 35 U.S.C. 154(b) by 148 days.

(21) Appl. No.: 16/981,322

(22) PCT Filed: Oct. 24, 2018

(86) PCT No.: PCT/CN2018/111746
§ 371 (c)(1),
(2) Date: Sep. 16, 2020

(87) PCT Pub. No.: WO2019/196380
PCT Pub. Date: Oct. 17, 2019

(65) Prior Publication Data
US 2021/0038414 A1 Feb. 11, 2021

(30) Foreign Application Priority Data

Apr. 12, 2018 (CN) .......................... 201810326731.3
Apr. 12, 2018 (CN) .......................... 201810336514.2

(51) Int. Cl.
*A61F 5/00* (2006.01)
(52) U.S. Cl.
CPC ................................ *A61F 5/0079* (2013.01)

(58) Field of Classification Search
CPC .... A61F 5/0036; A61F 5/0079; A61F 5/0076; A61F 5/0089; A61F 2002/045
See application file for complete search history.

(56) References Cited

U.S. PATENT DOCUMENTS 9,597,215 B2 3/2017 Chamorro, III et al.
2008/0221595 A1* 9/2008 Surti ..................... A61F 5/0079
606/151

(Continued)

FOREIGN PATENT DOCUMENTS

CN 106510895 * 3/2017
CN 106937898 A 7/2017

(Continued)

OTHER PUBLICATIONS

International Search Report (including English Translation) and Written Opinion with regard to PCT/CN2018/111746 dated Jan. 18, 2019.

(Continued)

*Primary Examiner* — Ariana Zimbouski
(74) *Attorney, Agent, or Firm* — BCF LLP

(57) ABSTRACT

A gastric diverter and a digestive tract support and a release method thereof. The digestive tract support has undeployed shape and deployed shape, and includes upper support, lower support and connecting member. In the deployed shape, a first opening is provided at top of the upper support, a second opening is provided at bottom thereof, and the lower support is disposed below the upper support; a third opening is provided at top of the lower support, a fourth (Continued)

opening is provided at bottom thereof, and the upper support and the lower support are connected by a plurality of connecting members; the fourth opening of the lower support is connected to a membrane tube, the deployed upper support and lower support both cannot pass through an open gastric pyloric orifice, and the connecting members can pass through the gastric pyloric orifice or be placed at the gastric pyloric orifice.

12 Claims, 5 Drawing Sheets

(56) References Cited

U.S. PATENT DOCUMENTS

| | | | |
|---|---|---|---|
| 2010/0305590 A1* | 12/2010 | Holmes | A61F 5/0079 606/151 |
| 2011/0004229 A1 | 1/2011 | Priplata et al. | |
| 2012/0184893 A1 | 7/2012 | Thompson et al. | |
| 2017/0252195 A1 | 9/2017 | Stangenes et al. | |

FOREIGN PATENT DOCUMENTS

| | | | |
|---|---|---|---|
| CN | 107126306 A | 9/2017 | |
| CN | 108635092 A | 10/2018 | |
| WO | WO-2008030403 A1 * | 3/2008 | ............... A61F 2/04 |

OTHER PUBLICATIONS

English Abstract for CN 108635092 retrieved on Espacenet on Sep. 8, 2020.
English Abstract for CN 107126306 retrieved on Espacenet on Sep. 8, 2020.
English Abstract for CN 106937898 retrieved on Espacenet on Sep. 8, 2020.
Notification of Grant with regard to the CN Patent Application No. 201810326731.3 dated May 12, 2020.
Office Action with regard to the CN Patent Application No. 201810326731.3 dated Oct. 29, 2019.
Communication with regard to the counterpart EP Patent Application No. 18914681.4 dated Aug. 20, 2021.

* cited by examiner

GASTRIC DIVERTER AND DIGESTIVE TRACT SUPPORT AND RELEASE METHOD THEREOF

CROSS-REFERENCE TO RELATED APPLICATIONS

The present application is a National Stage of International Application No. PCT/CN2018/111746, entitled "Gastric Diverter and Digestive Tract Support and Release Method Thereof," filed on Oct. 24, 2018, which claims priority to Chinese Patent Application number 201810336514.2, filed on Apr. 12, 2018, with the Chinese Patent Office, and Chinese Patent Application number 201810326731.3, filed on Apr. 12, 2018, with the Chinese Patent Office, the contents of each of which are incorporated herein by reference in their entirety.

TECHNICAL FIELD

The present disclosure relates to the technical field of medical devices, and in particular to a gastric diverter for treating endocrine diseases (such as diabetes, pancreatic islet dysfunction, and obesity) or diseases of the lower digestive tract (such as inflammation), and a gastrointestinal stent (i.e., digestive tract support) and a release method thereof.

BACKGROUND ART

It is known that diabetes is a disease to which people have gradually paid attention in recent years. It is one of the diseases of the rich. It is a non-infectious epidemic disease arising from the continuous improvement of the living standards of the modern civilized society, where people living better lives enjoy good and fine food with overnutrition, but their physical activity levels are reduced. Specifically, diabetes refers to a metabolic disease characterized by high blood sugar. It is caused by one or both of defective insulin secretion or impaired biological action thereof. Diabetes may lead to chronic damages and dysfunction of various tissues, especially eyes, kidneys, heart, blood vessels, and nerves. Diabetes is usually accompanied by obesity and many complications, which pose great threats to people's health. The data shows that in China alone, the incidence of diabetes is 9.7% among adults over 20 years old, and about 150 million people suffer from diabetes. It is known that diet control and increased exercise assisted by a certain drug therapy is the common way to ameliorate obesity and diabetes. However, this requires long-term persistence of patients, and relapse and weight regain are easily caused once diet control and exercise are stopped. Long-term administration of drugs or insulin also causes a heavy financial burden and inconvenience to the life of patients.

Another therapy is gastric bypass surgery. The gastric bypass surgery is very effective in the cure of type II diabetes and in the amelioration of obesity. In 2001, metabolic surgery (including gastric bypass surgery) is officially recommended by the International Diabetes Federation as a method for treating obesity combined with type II diabetes. However, the gastric bypass surgery which is a surgical procedure may cause wounds in human bodies, and thus is associated with many risks, such as death, intestinal obstruction, anastomotic leakage, pulmonary embolism, deep vein thrombosis, portal vein injury, risks in the respiratory system, etc.

Currently, diabetes is also treated in some foreign countries by implanting a structure similar to a gastric diverter or the like into the gastrointestinal tract. However, the gastric diverter has a complicated structure, and it is usually necessary to simultaneously operate multiple pull wires to achieve its function. Professional guidance is required before operation. An operator without rich experience may make an error in operation, increase discomfort of the patient, and thus have difficulty in operation. In addition, the gastric diverter is manufactured at high cost, and there is an additional problem of technical barriers. As a result, its widespread application in China is very difficult. Therefore, it is an urgent problem to be solved how to provide a method for treating diabetes that is carried out without causing much discomfort to a patient, or how to provide a device for treating diabetes with a simple structure, convenient operation, and low cost.

Currently, diabetes is also treated in some foreign countries and in China by implanting a product similar to the gastric diverter structure into the gastrointestinal tract. A soft catheter of a polymer material is implanted into the duodenum, and the soft catheter is generally fixed at the duodenal bulb by means of a small metal stent (or support). However, if a mesh stent made of a currently known material is not covered with a membrane, hyperplasia and adhesion are likely to occur, and it is difficult to remove the stent after it is implanted for a period of time. A stent covered with a membrane is very likely to fall off.

In the currently commercially available products manufactured by American GI companies and similar patent designs in China, the stents are each designed in a V shape with barbs and fixed at the duodenal bulb in the form of barbs. This design has the advantage of being adaptable to most patients, but there are also certain problems, because a design with too long barbs will cause perforation of the digestive tract while a design with too short barbs is likely to fall off. According to the clinical documents from the American GI companies, the design falls off at a rate about 10% in clinical use, and tearing and bleeding of the digestive tract will be caused at a certain percentage in the case of its removal, implantation, and accidental falling-off, therefore there is a certain risk in its use. If the catheter accidentally falls into the distal duodenum, jejunum, or even colon, intestinal obstruction is easily caused. Therefore, a better design is needed to avoid these risks.

Patent documents such as Patent Publication Nos. CN103298518, CN105263439, and WO2017/052694 disclose an intragastric device comprising: a porous structure comprising a top, a bottom, and an interior and being in a pre-expansion shape with a first volume and a post-expansion shape with a second volume greater than said first volume, wherein, in said post-expansion shape, said porous structure includes at least one first opening adjacent to said top and at least one second opening adjacent to said bottom, such that food enters said porous structure through said at least one first opening, passes through said interior, and exits said porous structure through said at least one second opening; and a sleeve having a flexible elongate body, a proximal end with a third opening, a distal end with a fourth opening, and a sleeve interior, wherein said sleeve is coupled to said porous structure, such that food exiting said at least one second opening enters said sleeve through said third opening, passes through said sleeve interior, and exits said sleeve through said fourth opening. The porous structure (stent) is expanded into a cylinder, ellipsoid, sphere, cube, or cuboid, occupies a considerable volume in the stomach and is movable freely in the stomach. The diameter of the porous structure is greater than the diameter of an opened pylorus. The sleeve (membrane tube) at the bottom of the porous structure extends through the pylorus to the duodenum. Said intragastric device further comprises an anti-migration component positioned at the junction of said porous structure and said sleeve and attached to said porous structure or said sleeve or both, wherein said anti-migration component comprises a compressed pre-expansion configuration and an expanded post-expansion configuration and is designed to sit proximal to a patient's pylorus and prevent migration of said porous structure into and through said pylorus. In the structure described above, the spherical stent is wholly positioned inside the stomach and outside the pylorus, and the sleeve (membrane tube) is positioned in the pylorus. The main mechanism of action is as follows. A meshed spherical device woven from a memory alloy is implanted in the stomach. The spherical stent is covered with a membrane. The spherical stent occupies a certain volume in the stomach and may generate a feeling of satiety, and food can be stored in the spherical stent for a certain period of time, thereby reducing food intake and achieving the effect of treating metabolic diseases such as obesity and diabetes. The membrane tube for drainage of food is its secondary functional structure. However, the above-mentioned intragastric device has the following problems. Firstly, the self-expanding memory alloy material has a certain mechanical force and weight, thus the intragastric device with a size large enough to occupy the internal volume of the stomach will apply a certain pressure to the stomach and will oppress the gastric mucosa and is very likely to cause ulcers of digestive tract when implanted in the stomach. Secondly, food stays in the balloon for a long time. Although this can slow gastric emptying, the growth of bacteria may be easily caused to induce an inflammatory response. Thirdly, the device is not fixed in the pyloric orifice or in the duodenal bulb, thus the lower extended membrane tube is very likely to move back into the stomach due to the reverse peristalsis of the digestive tract, causing food not to flow according to the designed channel. Fourthly, the membrane tube located at the pyloric orifice has a relatively large size and thus may lead to an obvious foreign body sensation in the pylorus and may easily cause conditions such as poor closure of the pylorus and bile regurgitation, especially after food is contained therein.

Patent documents such as Patent Publication Nos. CN102335052, CN104382671, CN204671331, and CN205359721 disclose a gastrointestinal stent, comprising a main body formed by connecting a plurality of support units with certain rigidity and supporting function, and easily-bendable connecting components. The two ends of the connecting component are connected to the corresponding support units, respectively. The main body is in an easily-bendable straight cylindrical structure or an easily-bendable composite structure consisting of a cylinder and a cone. The support unit is in an integral structure formed by carving a metal pipe, or a structure formed by weaving a wire material. The connecting components are formed by weaving metal threads or plastic threads with good softness, and the connecting threads are generally woven perpendicular to the plane of the upper and lower supports. The stent is used for the treatment of stenosis or obstruction of the digestive tract and serves the function of expanding and supporting the stenosis. It is generally implanted as an independent product into the digestive tract without being connected to a membrane tube, and cannot be used in the pyloric orifice of the stomach or as a gastric diverter because of its high supporting strength and difficulty in deformability.

SUMMARY

Technical Problems

An object of the present disclosure is to provide a gastric diverter, and a gastrointestinal stent and a release method thereof. The stent consists of two parts, wherein one part is fixed at the pyloric orifice of the stomach and the other part is fixed at the duodenal bulb. The stent can provide a certain supporting force, but also has a certain flexibility. It can be ensured by the stent that an opening of an upper segment of a membrane tube which is an extension segment is fixed at the duodenal bulb and can be opened and closed with the opening and closing of the intestinal tract without causing damage to the intestinal wall. The extended membrane tube can treat metabolic diseases such as diabetes and obesity by isolating food. The stent has good applicability, is fabricated by convenient processes with low cost at a fast production rate, and thus is used as a stent in the digestive tract. The stent may also be connected to an implantable catheter.

SOLUTIONS TO THE PROBLEMS

Technical Solutions

In view of the above-mentioned problems in the prior art, the inventors of the present disclosure have designed a double-segment stent after careful research. The stent is woven from an elastic wire material, has two sides to be fixed at the pyloric orifice and the duodenal bulb, and is covered with a membrane on its outer layer to prevent tissue hyperplasia. The stent can fully solve the problem of easy fall-off of the stent and the membrane tube or easy hyperplasia, and causes no damage to human tissue because of its smooth outer edge. Thus, the present disclosure has been completed.

Specifically, the following technical solutions are employed in the present disclosure.

A gastrointestinal stent of a gastric diverter, the gastrointestinal stent being in a pre-expansion shape and a post-expansion shape, comprising an upper support, a lower support, and a connecting member, wherein in the post-expansion shape, the upper support is provided with a first opening adjacent to its top and a second opening adjacent to its bottom, the lower support is disposed below the upper support, the lower support is provided with a third opening adjacent to its top and a fourth opening adjacent to its bottom, the upper support and the lower support are connected by several connecting members, the fourth opening of the lower support is connected to a membrane tube, and both of the extended upper support and lower support cannot pass through an opened pyloric orifice of a stomach (in other words, the outer diameter of each of the extended upper support and lower support is greater than the outer diameter of the opened pyloric orifice of the stomach) and the connecting member can pass through the pyloric orifice of the stomach or be placed through the pyloric orifice of the stomach. In this way, the stent is fixed in two parts, wherein one part (the upper support) is fixed at the pyloric orifice of the stomach, so that the upper end of the membrane tube is firmly positioned in the digestive tract during peristalsis of the digestive tract, and the other part (the lower support) is fixed at the duodenal bulb, so as to avoid easy movement of the lower extended membrane tube back into the stomach during reverse peristalsis of the digestive tract, which would cause food not to flow according to the designed channel. The stent can provide a certain supporting force, but also has a certain flexibility. It can be ensured by the stent that the opening of the upper segment of the membrane tube which is an extension segment is fixed at the duodenal bulb and can be opened and closed with the opening and closing of the intestinal tract without causing damage to the intestinal wall. The extended membrane tube can treat metabolic diseases such as diabetes and obesity by isolating food. The stent has good applicability, is fabricated by convenient processes with low cost at a fast production rate, and thus is used as a stent in the digestive tract. The stent may also be connected to an implantable catheter.

Preferably, the connecting member is a connecting thread. The connecting thread may be in the shape of a line or of a thin strip with a small cross-sectional area, so that the connection of the upper and lower supports can be ensured without affecting the flow of food. In addition, in other embodiments, the connecting member may be a flexible membrane tube, an elastic tube with a mesh structure, a flexible or elastic connecting band or connecting sheet, or the like. However, these connecting members having relatively large sizes, even if they are reduced, may cause poor closure of the pylorus of the stomach and cause discomfort to patients, therefore the connecting thread is preferred. The connecting thread may be a metal wire such as nickel-titanium alloy, Type 304 stainless steel, or the like, or may be a wire made of a polymer material with good elasticity and fatigue resistance, such as polyethylene, nylon, and other materials.

Preferably, the connecting thread is externally covered with a membrane. In this way, the connecting thread is isolated from contact with tissue in the digestive tract to reduce frictional damage and reduce the probability of occurring gastric ulcers. The connecting thread is externally covered with a film-like elastic material to prevent damage of the pyloric ring by an excessively sharp connecting wire. Preferably, the covering film-like elastic material may be one or more materials selected from silicone, polyurethane, etc.

Preferably, the connecting member includes a plurality of connecting threads, the upper ends of the plurality of connecting threads are connected to the upper support, respectively, and the lower ends of the plurality of connecting threads are connected to the lower support, respectively. In this way, the upper and lower supports are connected by using the plurality of connecting threads, so that the force is distributed more uniformly, and the upper and lower supports are fixed more reliably.

Preferably, the connecting member will be elastically deformed to be bent or have a reduced outer diameter in conformity with a pyloric orifice of a human body in a natural state at its position corresponding to the pyloric orifice of the stomach. In this way, after the connecting member is shaped, when the pylorus of the stomach of a human body is in a substantially closed state, the connecting member can be in a natural stretchable shape in conformity with the structure of the pyloric orifice of the human body and its lower part, without expanding the pylorus and causing damage to the pyloric structure. The connecting member can be stretched when it is subjected to an upward or downward pulling force, but it has a shape memory function and can be restored to its original shape when the upward or downward pulling force disappears.

Preferably, the upper support is in the shape of a cone, an inverted cone, a straight cylinder, or a straw hat. In this way, the upper support is in the shape of a rectangle, a trapezoid, or a shape similar to a rectangle or a trapezoid with two curved lateral sides, when viewed in vertical section. The first opening, the second opening, and the exposed corners of the upper support may be rounded to avoid damage to tissue. Of course, in other embodiments, the upper support may be in a spherical shape or other shapes.

Preferably, the outer diameter of the second opening of the upper support is greater than the outer diameter of the first opening. In this way, the upper support is characterized by having a larger opening at the lower end, which can be stuck in the pyloric orifice without damaging the pyloric tissue. The upper support has two, upper and lower, openings through which food can pass, but it does not have the function of storing food. The function of the upper support is to be stuck in the pyloric orifice, pull and hold the lower support, and indirectly pull and hold the membrane tube in the duodenum to avoid downward movement or even discharge of the membrane tube during the peristalsis of the digestive tract. The lower opening of the upper support has a diameter greater than the diameter of the pyloric orifice, and preferably has a diameter of 20 to 50 mm. The upper opening preferably has a diameter of 20 to 30 mm. The upper support 1 preferably has a height of 5 to 15 mm.

Preferably, the lower support is in a cylindrical structure. The lower support structure is located inside the pyloric orifice, specifically in the duodenal bulb. The main function of the structure is to provide the extended membrane tube with an opening through which food can enter the membrane tube. Its second function is to prevent movement of the membrane tube from the duodenum back into the stomach and fix the position of the membrane tube in cooperation with the upper support. Thirdly, the upper and lower supports are positionally restricted to the inside and outside of the pyloric orifice of the stomach, respectively, so that the upper support cannot move freely in the stomach and is connected to the lower support and the membrane tube, and the upper support can be slightly displaced only at the pyloric orifice to avoid discomfort. The upper opening (third opening) and the lower opening (fourth opening) of the lower support preferably have the same outer diameters, so that the lower support is in a straight cylindrical shape. When viewed in vertical section, the lower support is in the shape of a rectangle or a rounded rectangle, which may be somewhat rounded at upper and lower corners for the main purpose of preventing damage to tissue. However, the upper opening (third opening) and the lower opening (fourth opening) of the lower support may have different outer diameters. In other words, the lower support may have a side wall tapered or curved to a certain degree, so as to be adapted to the structure of the duodenal bulb and easily connected to the membrane tube.

Preferably, the lower support has a diameter of 15 to 25 cm, which matches the diameter of the duodenal bulb of the human body. The lower support has a height of 5 to 20 mm, preferably 10 mm, which is a height set as small as possible to reach the maximum limit for comfort of the human body under the premise of satisfying the above functions.

There is a distance of 20 to 60 mm between the lower end of the upper support and the upper end of the lower support. An appropriate dimension is preferably selected depending on different anatomical structures of human bodies, based on the principle that it should be greater than the height of the pyloric ring and the lower end of the lower support should be kept away from the duodenal papilla.

The upper and lower supports are in mesh structures and may be formed by a process of weaving or cutting. The mesh structure may be in a variety of shapes such as a diamond shape, a honeycomb shape, and a zigzag shape. This structure allows the stent to be compressed and expanded freely in the transverse and longitudinal directions and to have good elasticity. Preferably, both the upper support and the lower support are woven from elastic wires, and the outer surface of the elastic wire are covered with membrane, or the entire outer surfaces of the upper support and the lower support are covered with membranes, respectively. This can isolate the wire materials of the stent from contact with tissue in the stomach, so as to reduce frictional damage, reduce the probability of occurring gastric ulcers, and prevent tissue hyperplasia. The polymer material membrane may be made of one or more of medical materials such as silicone, TPU, and TPE. The woven wires are biocompatible elastic wires, and may be metal wires, wires made of polymer materials, or wires made of degradable materials.

The lower support is fixedly connected to the membrane tube by sewing, hot pressing, ultrasonic welding, or laser welding.

Preferably, the upper end of the connecting thread is fixedly connected to a position of the top of the upper support near the first opening, and the lower end of the connecting thread is fixedly connected to a position of the top of the lower support near the third opening. In such a preferred mode, the bottom of the upper support can be prevented from being contracted to affect the fixation when the gastrointestinal stent is subjected to the upward and downward pulling forces. Moreover, the bottom of the upper support contacts and supports the outside of the pyloric orifice of the stomach with an elastic surface, which can reduce or avoid damage of tissue in the digestive tract by the connecting threads and the upper support.

Preferably, the upper end of the connecting thread is fixedly connected to a position of the top of the upper support near the first opening, the connecting thread passes through a mesh woven in the middle of the upper support, and then the lower end of the connecting thread is fixedly connected to a position of the top of the lower support near the third opening. In such a further preferred mode, the upper support can be prevented from turning upside down to affect the fixation when the gastrointestinal stent is subjected to the upward and downward pulling forces. Moreover, the upper support contacts and supports the outside of the pyloric orifice of the stomach with an elastic surface, which can reduce or avoid damage of tissue in the digestive tract.

Preferably, the upper support and the lower support are provided with developing rings, so that the stent can be positioned under X-rays, and the developing ring is preferably made of platinum, gold, tantalum, or the like.

Preferably, the upper support is provided with an upper support retrieving thread, and the lower support is provided with a lower support retrieving thread. In this way, the gastrointestinal stent and the membrane tube can be removed by a specially-made retriever or by grasping forceps for endoscope.

A gastric diverter is characterized by comprising the gastrointestinal stent as described above.

A gastric diverter comprises a storage tube shell, a release body, and a delivering component, and is characterized in that the storage tube shell is in a tubular shape, the storage tube shell is opened at both ends, a membrane tube and an above-mentioned gastrointestinal stent, which are to be released and in a folded state, are disposed in the storage tube shell, the release body is disposed at the distal opening of the storage tube shell and is connected to an end of the membrane tube, and the release body is made of a material that can be digested, absorbed, or dissolved by the intestinal tract of a human body. The delivering component comprises an inner tube, a middle tube, and an outer tube which are sequentially sleeved on one another and are movable relative to one another. A part of the inner tube is located in the storage tube shell and is connected to the release body; one end of the middle tube extends into the storage tube shell through the proximal opening of the storage tube shell, and a pushing block located in the storage tube shell for pushing against the membrane tube is fixedly disposed at the end of the middle tube; the outer tube is located outside the storage tube shell and has one end fixedly connected directly or indirectly to the proximal opening of the storage tube shell, wherein the inner tube is moved toward an operator along its axial direction, so that the release body is detached from the storage tube shell, and the inner tube and the middle tube drive the membrane tube to be detached from the storage tube shell, expanded, and released.

Preferably, the storage tube shell is provided with a marking line, which is positioned 2 to 5 cm away from the distal opening of the storage tube shell. In this way, it is convenient to release the two, upper and lower, supports inside and outside the pyloric orifice, respectively.

Preferably, the release body comprises a release body shell and a release body core. The release body shell is disposed at the distal opening of the storage tube shell. The release body core is connected to the inner tube. The release body shell is wrapped around the release body core.

A method for releasing a gastric diverter includes the gastric diverter as described above and the steps of:
1) disposing the membrane tube and the gastrointestinal stent in the folded state in the storage tube shell, and closing the distal opening of the storage tube shell by the release body;
2) delivering the release body at the distal end of the storage tube shell into the duodenum under the guidance of a guide wire, and then pushing the release body and the membrane tube out of the storage tube shell;
3) withdrawing the storage tube shell until the marking line reaches the pyloric orifice, pushing the lower support out of the storage tube shell to leave the lower support in the duodenal bulb; and
4) further withdrawing the storage tube shell, pushing the upper support out of the storage tube shell to leave the upper support outside the pyloric orifice to complete the release.

ADVANTAGEOUS EFFECTS OF THE PRESENT DISCLOSURE

Advantageous Effects

According to the above technical solutions employed in the present disclosure, the upper support of the gastrointestinal stent can be fixed at the pyloric orifice, and the lower support can be fixed at the duodenal bulb, so that it is ensured that the membrane tube can be stably fixed in the duodenum for a long time without damaging human tissue. Moreover, the outer layer of the stent is covered with a membrane, which can reduce the friction between the stent and the tissue, so as to avoid tissue hyperplasia caused by long-term implantation of the stent, and facilitate the later removal of the stent. Furthermore, the upper support fixed at the pyloric orifice has one end with an opening positioned at the pyloric orifice and the other end with an opening positioned in the stomach, thus the gastric emptying can also be delayed. The stent has a better therapeutic effect in the treatment of metabolic diseases such as diabetes and obesity compared with the traditional gastric diverters or duodenal cannulas. The stent has good applicability and is fabricated by convenient processes with low cost at a fast production rate. The stent is connected to a gastrointestinal membrane tube. The stent of the present disclosure can be implanted in the digestive tract for the treatment of endocrine diseases such as diabetes, pancreatic islet dysfunction, and obesity, or diseases of the lower digestive tract such as inflammation. Compared with the prior art, the stent of the present disclosure can effectively prevent tissue hyperplasia after implantation and can be fixed at the pyloric orifice and at the duodenal papilla for a long time without causing damage to the digestive tract of a human body. Moreover, the stent has the advantages of having good structural applicability, being fabricated by convenient processes with low cost at a fast production rate, having guaranteed quality, and being manufactured conveniently. Furthermore, the stent is implanted with good comfort and compliance without causing harm to human tissue. In addition, the stent may also be connected to an implantable membrane tube. After the stent is connected to the membrane tube, the irritation to the digestive tract can be reduced, and it is safer and more convenient to pull, adjust, or retrieve the stent.

Figure 1:
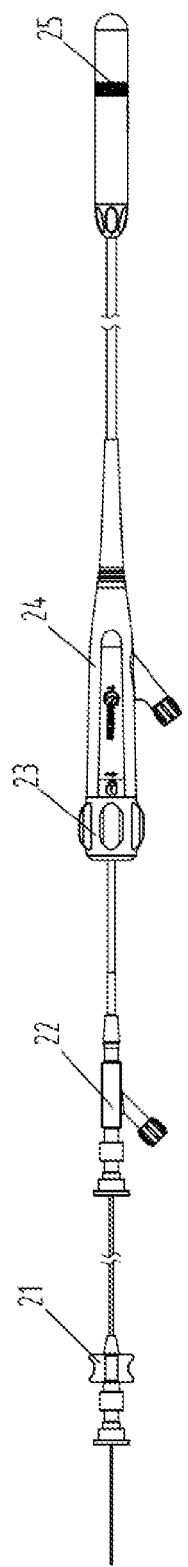
FIG. 1 is a schematic structural view of a gastric diverter of the present disclosure.

DESCRIPTION OF REFERENCE NUMERALS 1-upper support; 2-lower support; 3-connecting thread; 4-elastic wire; 5-support covering membrane; 6-developing ring; 7-membrane tube; 8-upper support retrieving thread; 9-lower support retrieving thread; 11-release body shell; 12-release body core; 13-storage tube shell; 14-pushing block; 15-nut; 16-outer tube; 17-middle tube; 18-inner tube; 21-rear handle; 22-middle handle; 23-limit ball head; 24-front handle; 25-marking line; 101-stomach; 102-pyloric orifice; 103-duodenal bulb; 104-duodenal papilla; 105-duodenum; 106-jejunum.

DETAILED DESCRIPTION OF EMBODIMENTS

Embodiments of the present disclosure will be described below in detail. Examples of the embodiments are shown in the drawings, throughout which the same or similar reference numerals indicate the same or similar elements or elements having the same or similar functions. The embodiments described below with reference to the drawings are exemplary and are intended to explain the present disclosure, and should not be construed as limiting the present disclosure.

In the description of the present disclosure, it should be understood that orientation or positional relationships indicated by the terms such as "center", "longitudinal", "transverse", "length", "width", "thickness", "up", "down", "front", "rear", "left", "right", "vertical", "horizontal", "top", "bottom", "inside", "clockwise", and "anticlockwise" are the orientation or positional relationships shown based on the drawings, and these terms are intended only to facilitate the description of the present disclosure and simplify the description, but not intended to indicate or imply that the referred devices or elements must be in a particular orientation, or constructed or operated in the particular orientation, and therefore should not be construed as limiting the present disclosure.

In addition, the terms "first" and "second" are used for descriptive purposes only, and should not be understood as an indication or implication of relative importance or an implicit indication of the number of the indicated technical features. Thus, a feature defined with the terms "first" and "second" may explicitly or implicitly include one or more such features. In the description of the present disclosure, "a plurality of" means two or more unless otherwise expressly and specifically defined.

In the present disclosure, terms such as "mount", "couple", "connect" and "fix" should be understood broadly unless otherwise expressly specified or defined. For example, connection may be fixed connection or detachable connection or integral connection, may be mechanical connection or electric connection, and may be direct coupling or indirect coupling via an intermediate medium or internal communication between two elements. The specific meanings of the above-mentioned terms in the present disclosure can be understood by those of ordinary skill in the art according to specific situations.

In the present disclosure, unless otherwise expressly specified or defined, a first feature "on" (or above) or "below" a second feature may include a case where the first and second features are in direct contact, and may also include a case where the first and second features are not in direct contact, but are in contact via an additional feature therebetween. Moreover, a first feature "on", "above", or "over" a second feature is meant to include a case where the first feature is directly above or obliquely above the second feature, or merely means that the first feature is at a level height higher than the second feature. A first feature "under", "below", or "underneath" a second feature is meant to include a case where the first feature is directly below or obliquely below the second feature, or merely means that the first feature is at a level height lower than the second feature.

Figure 2:
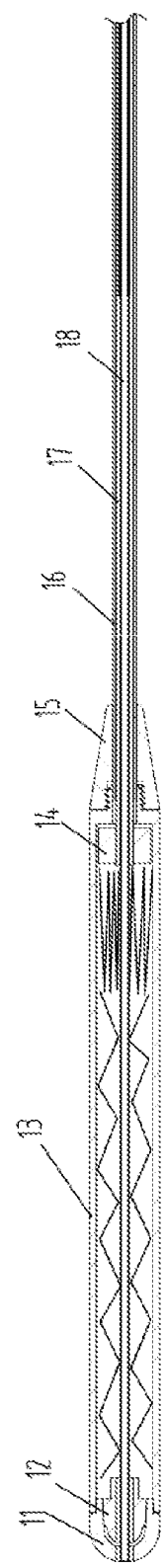
FIG. 2 is an enlarged schematic structural view of a distal end of the gastric diverter of the present disclosure.
Figure 3:
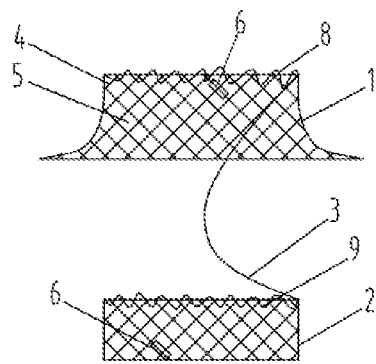
FIG. 3 is a side view of an expanded structure of a first embodiment of a gastrointestinal stent of the present disclosure (a single-thread straw-hat-shaped stent)
Figure 4:
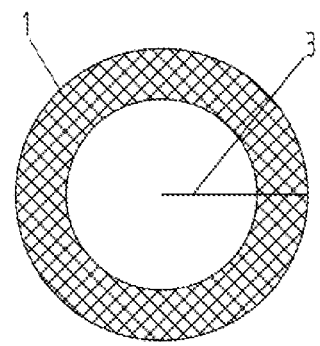
FIG. 4 is a front view of the expanded structure of the first embodiment of the gastrointestinal stent of the present disclosure (a single-thread straw-hat-shaped stent)
Figure 5:
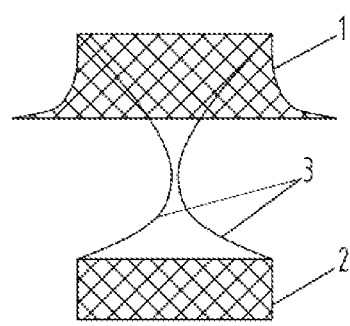
FIG. 5 is a side view of an expanded structure of a second embodiment of a gastrointestinal stent of the present disclosure (a double-thread straw-hat-shaped stent)
Figure 6:
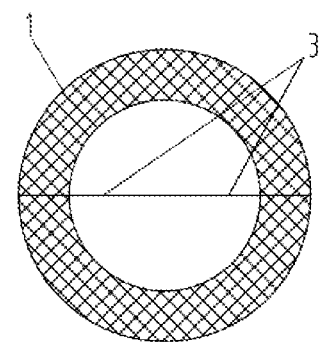
FIG. 6 is a front view of the expanded structure of the second embodiment of the gastrointestinal stent of the present disclosure (a double-thread straw-hat-shaped stent)
Figure 7:
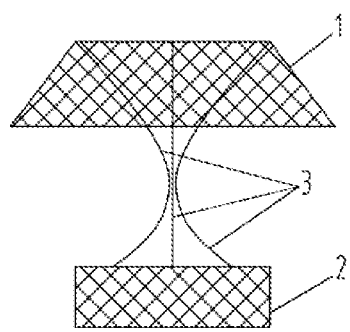
FIG. 7 is a side view of an expanded structure of a third embodiment of a gastrointestinal stent of the present disclosure (a three-thread trapezoidal stent)
Figure 8:
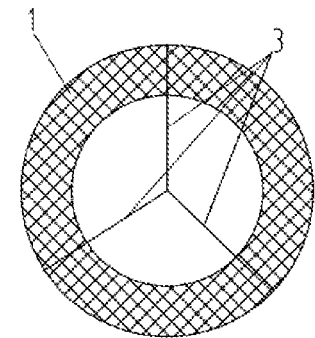
FIG. 8 is a front view of the expanded structure of the third embodiment of the gastrointestinal stent of the present disclosure (a three-thread trapezoidal stent)
Figure 9:
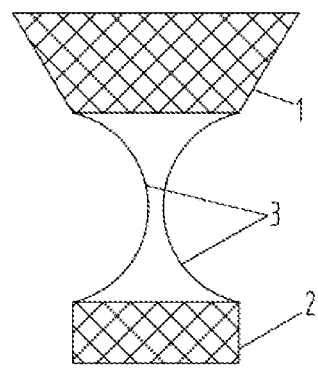
FIG. 9 is a side view of an expanded structure of a fourth embodiment of a gastrointestinal stent of the present disclosure (a double-thread inverted trapezoidal stent)
Figure 10:
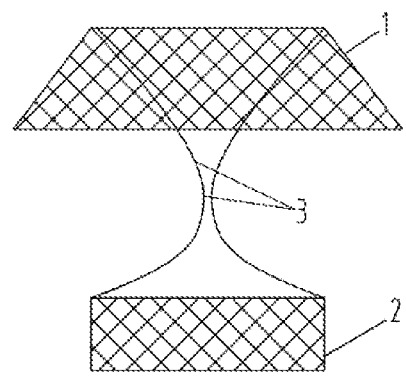
FIG. 10 is a side view of an expanded structure of a fifth embodiment of a gastrointestinal stent of the present disclosure (a double-thread trapezoidal stent)
Figure 11:
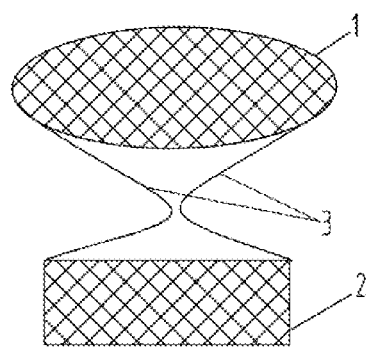
FIG. 11 is a side view of an expanded structure of a sixth embodiment of a gastrointestinal stent of the present disclosure (a double-thread arc-shaped stent)
Figure 12:
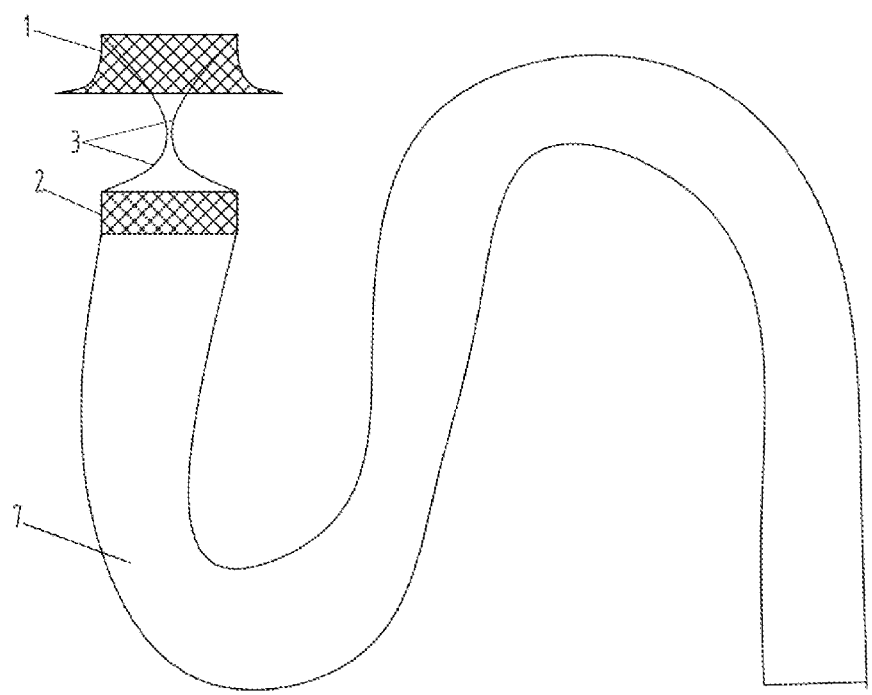
FIG. 12 is a schematic view of an expanded structure of a membrane tube and a gastrointestinal stent of the present disclosure.
Figure 13:
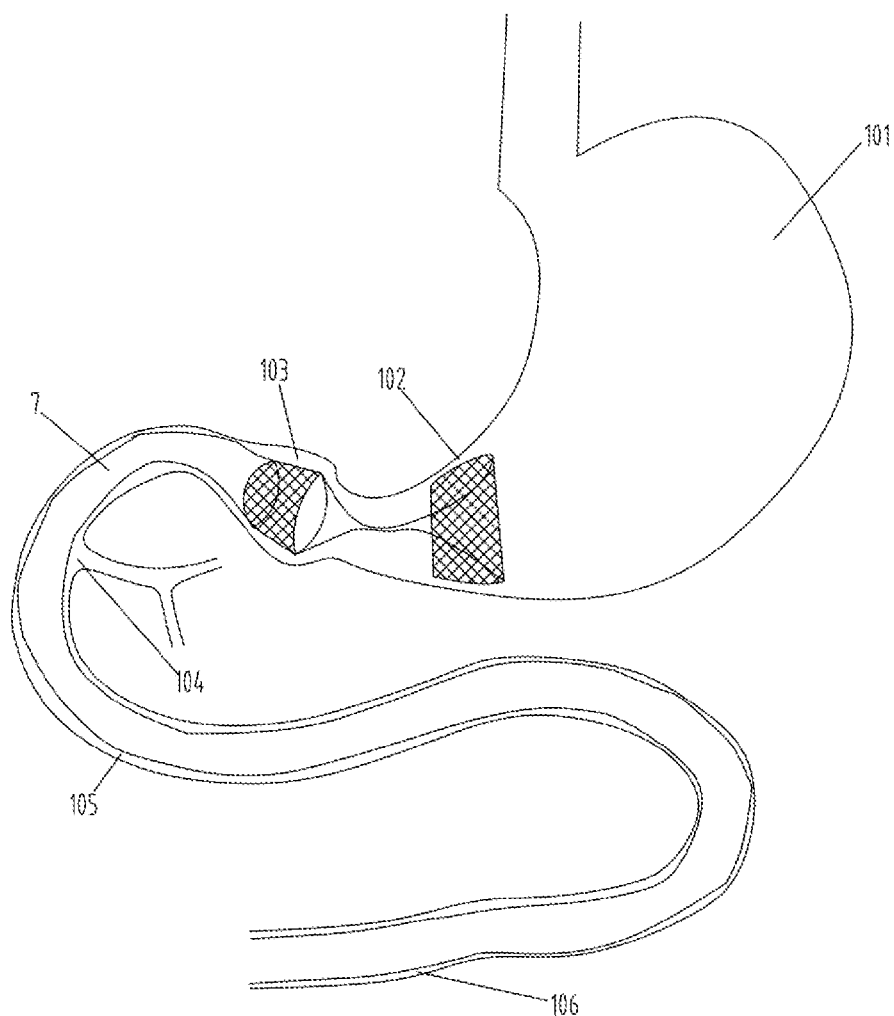
FIG. 13 is a schematic view of the membrane tube and the gastrointestinal stent of the present disclosure placed in the digestive tract of a human body.

A gastric diverter as shown in FIGS. 1 and 2 comprises a storage tube shell 13, a release body, and a delivering component. The storage tube shell 13 is in a tubular shape. The storage tube shell 13 is opened at both ends. A membrane tube 7 and a gastrointestinal stent to be released in a folded state are disposed in the storage tube shell 13. The release body is disposed at the distal opening of the storage tube shell 13 and is connected to an end of the membrane tube 7. The release body is made of a material that can be digested, absorbed, or dissolved by the intestinal tract of a human body. The delivering component comprises an inner tube 18, a middle tube 17, and an outer tube 16 which are sequentially sleeved on one another and are movable relative to one another. A part of the inner tube 18 is located in the storage tube shell 13 and is connected to the release body; one end of the middle tube 17 extends into the storage tube shell 13 through the proximal opening of the storage tube shell 13, and a pushing block 14 located in the storage tube shell 13 for pushing against the membrane tube 7 is fixedly disposed at the end of the middle tube 17; the outer tube 16 is located outside the storage tube shell 13 and has one end fixedly connected directly or indirectly to the proximal opening of the storage tube shell 13, wherein the inner tube 18 is moved toward an operator along its axial direction, so that the release body is detached from the storage tube shell 13, and the inner tube 18 and the middle tube 17 drive the membrane tube 7 to be detached from the storage tube shell 13, expanded and released.

The storage tube shell 13 is provided with a marking line 25, which is positioned 2 to 5 cm away from the distal opening of the storage tube shell 13. The release body comprises a release body shell 11 and a release body core 12. The release body shell 11 is disposed at the distal opening of the storage tube shell 13. The release body core 12 is connected to the inner tube 18. The release body shell 11 is wrapped around the release body core 12.

FIGS. 3 to 11 show a gastrointestinal stent of a gastric diverter. The gastrointestinal stent has a pre-expansion shape and a post-expansion shape and comprises an upper support 1, a lower support 2, and a connecting member 3. In the post-expansion shape, the upper support 1 is provided with a first opening adjacent to its top and a second opening adjacent to its bottom, the lower support 2 is disposed below the upper support 1, the lower support 2 is provided with a third opening adjacent to its top and a fourth opening adjacent to its bottom, the upper support 1 and the lower support 2 are connected by several connecting members 3, the fourth opening of the lower support 2 is connected to a membrane tube 7, and both of the expanded upper support 1 and lower support 2 cannot pass through an opened pyloric orifice of a stomach (in other words, the outer diameter of each of the expanded upper support 1 and lower support 2 is greater than the outer diameter of the opened pyloric orifice of the stomach) and the connecting member 3 can pass through the pyloric orifice of the stomach or be placed through the pyloric orifice of the stomach. In this way, the stent is fixed in two parts, wherein one part (the upper support) is fixed at the pyloric orifice of the stomach, so that the upper end of the membrane tube is firmly positioned in the digestive tract during peristalsis of the digestive tract, and the other part (the lower support) is fixed at the duodenal bulb, so as to avoid easy movement of the lower extended membrane tube back into the stomach during reverse peristalsis of the gastrointestinal tract, which would cause food not to flow according to the designed channel. The stent can provide a certain supporting force, but also has a certain flexibility. It can be ensured by the stent that the opening of the upper segment of the membrane tube which is an extension segment is fixed at the duodenal bulb and can be opened and closed with the opening and closing of the intestinal tract without causing damage to the intestinal wall. The extended membrane tube can treat metabolic diseases such as diabetes and obesity by isolating food. The stent has good applicability, is fabricated by convenient processes with low cost at a fast production rate, and thus is used as a stent in the digestive tract. The stent may also be connected to an implantable catheter.

The connecting member 3 is a connecting thread. The connecting thread may be in the shape of a line or of a thin strip with a small cross-sectional area, so that the connection of the upper and lower supports can be ensured without affecting the flow of food. In addition, in other embodiments, the connecting member may be a flexible membrane tube, an elastic tube with a mesh structure, a flexible or elastic connecting band or connecting sheet, or the like. However, these connecting members having relatively large sizes, even if they are reduced, may cause poor closure of the pylorus of the stomach and cause discomfort to patients, therefore the connecting thread is preferred. The connecting thread may be a metal wire, such as nickel-titanium alloy, Type 304 stainless steel, or the like, or may be a wire made of a polymer material with good elasticity and fatigue resistance, such as polyethylene, nylon, and other materials.

The connecting thread is externally covered with a membrane. In this way, the connecting thread is isolated from contact with tissue in the digestive tract to reduce frictional damage and reduce the probability of occurring gastric ulcers. The connecting thread is externally covered with a film-like elastic material to prevent damage of the pyloric ring by an excessively sharp connecting wire. Preferably, the covering film-like elastic material may be one or more materials selected from silicone, polyurethane, etc.

The connecting member 3 includes a plurality of connecting threads, the upper ends of the plurality of connecting threads are connected to the upper support 1, respectively, and the lower ends of the plurality of connecting threads are connected to the lower support 2, respectively. In this way, the upper and lower supports are connected by using the plurality of connecting threads, so that the force is distributed more uniformly, and the upper and lower supports are fixed more reliably.

The connecting member 3 will be elastically deformed to be bent or have a reduced outer diameter in conformity with a pyloric orifice of a human body in a natural state at a position corresponding to the pyloric orifice of the stomach. In this way, after the connecting member is shaped, when the pylorus of the stomach of a human body is in a substantially closed state, the connecting member can be in a natural stretchable shape in conformity with the structures of the pyloric orifice of the human body and its lower part, without expanding the pylorus and causing damage to the pyloric structure. The connecting member can be stretched when it is subjected to an upward or downward pulling force, but it has a shape memory function and can be restored to its original shape when the upward or downward pulling force disappears.

The upper support 1 is in the shape of a cone, an inverted cone, a straight cylinder, or a straw hat. In this way, the upper support is in the shape of a rectangle, a trapezoid, or a shape similar to a rectangle or a trapezoid with two curved lateral sides, when viewed in vertical section. The first opening, the second opening, and the exposed corners of the upper support may be rounded to avoid damage to tissue. Of course, in other embodiments, the upper support may be in a spherical shape or other shapes.

The outer diameter of the second opening of the upper support 1 is greater than the outer diameter of the first opening. In this way, the upper support is characterized by having a larger opening at the lower end, which can be stuck in the pyloric orifice without damaging the pyloric tissue. The upper support has two, upper and lower, openings through which food can pass, but it does not have the function of storing food. The function of the upper support is to be stuck in the pyloric orifice, pull and hold the lower support, and indirectly pull and hold the membrane tube in the duodenum, to avoid downward movement or even discharge of the membrane tube during the peristalsis of the digestive tract. The lower opening of the upper support has a diameter greater than the diameter of the pyloric orifice, and preferably has a diameter of 20 to 50 mm. The upper opening preferably has a diameter of 20 to 30 mm. The upper support 1 preferably has a height of 5 to 15 mm.

The lower support is in a cylindrical structure. The lower support structure is located inside the pyloric orifice, specifically in the duodenal bulb. The main function of the structure is to provide the extended membrane tube with an opening through which food can enter the membrane tube. Its second function is to prevent movement of the membrane tube from the duodenum back into the stomach and fix the position of the membrane tube in cooperation with the upper support. Thirdly, the upper and lower supports are positionally restricted to the inside and outside of the pyloric orifice of the stomach, respectively, so that the upper support cannot move freely in the stomach and is connected to the lower support and the membrane tube, and the upper support can be slightly displaced only at the pyloric orifice to avoid discomfort. The upper opening (third opening) and the lower opening (fourth opening) of the lower support preferably have the same outer diameters, so that the lower support is in a straight cylindrical shape. When viewed in vertical section, the lower support is in the shape of a rectangle or a rounded rectangle, which may be somewhat rounded at upper and lower corners for the main purpose of preventing damage to tissue. However, the upper opening (third opening) and the lower opening (fourth opening) of the lower support may have different outer diameters. In other words, the lower support may have a side wall tapered or curved to a certain degree, so as to be adapted to the structure of the duodenal bulb and easily connected to the membrane tube.

The lower support has a diameter of 15 to 25 cm, which matches the diameter of the duodenal bulb of the human body. The lower support has a height of 5 to 20 mm, preferably 10 mm, which is a height set as small as possible to reach the maximum limit for comfort of the human body under the premise of satisfying the above functions.

The upper end of the connecting thread is fixedly connected to a position of the top of the upper support 1 near the first opening, and the lower end of the connecting thread is fixedly connected to a position of the top of the lower support 2 near the third opening. In such a preferred mode, the bottom of the upper support can be prevented from being contracted to affect the fixation when the gastrointestinal stent is subjected to the upward and downward pulling forces. Moreover, the bottom of the upper support contacts and supports the outside of the pyloric orifice of the stomach with an elastic surface, which can reduce or avoid damage of tissue in the digestive tract by the connecting thread(s) and the upper support.

The upper end of the connecting thread is fixedly connected to a position of the top of the upper support 1 near the first opening, the connecting thread passes through a mesh woven in the middle of the upper support 1, and then the lower end of the connecting thread is fixedly connected to a position of the top of the lower support 2 near the third opening. In such a further preferred mode, the upper support can be prevented from turning upside down to affect the fixation when the gastrointestinal stent is subjected to the upward and downward pulling forces. Moreover, the upper support contacts and supports the outside of the pyloric orifice of the stomach with an elastic surface, which can reduce or avoid damage of tissue in the digestive tract.

There is a distance of 20 to 60 mm between the lower end of the upper support and the upper end of the lower support. An appropriate dimension is preferably selected depending on different anatomical structures of human bodies, based on the principle that it should be greater than the height of the pyloric ring and the lower end of the lower support should be kept away from the duodenal papilla.

The upper and lower supports are in mesh structures and may be formed by a process of weaving or cutting. The mesh structure may be in a variety of shapes such as a diamond shape, a honeycomb shape, and a zigzag shape. This structure allows the stent to be compressed and expanded freely in the transverse and longitudinal directions and to have good elasticity. Preferably, both the upper support 1 and the lower support 2 are woven from elastic wires 4, and the outer surface of the elastic wire 4 is covered with membrane, or the entire outer surfaces of the upper support 1 and the lower support 2 are covered with membranes, respectively. This can isolate the wire materials of the stent from contact with tissue in the stomach, so as to reduce frictional damage, reduce the probability of occurring gastric ulcers, and prevent tissue hyperplasia. The polymer material membrane may be made of one or more of medical materials such as silicone, TPU, and TPE. The woven wires are biocompatible elastic wires, and may be metal wires, wires made of polymer materials, or wires made of degradable materials.

The lower support is fixedly connected to the membrane tube by one or more of hot melting, hot pressing, ultrasonic welding, high-frequency welding, sewing, laser welding, or the like.

Preferably, the upper end of the connecting thread is fixedly connected to a position of the top of the upper support 1 near the first opening, and the lower end of the connecting thread is fixedly connected to a position of the top of the lower support 2 near the third opening. In such a preferred mode, the bottom of the upper support can be prevented from being contracted and affecting the fixation when the gastrointestinal stent is subjected to the upward and downward pulling forces. Moreover, the bottom of the upper support contacts and supports the outside of the pyloric orifice of the stomach with an elastic surface, which can reduce or avoid damage of tissue in the digestive tract by the connecting thread(s) and the upper support.

Preferably, the upper end of the connecting thread is fixedly connected to a position of the top of the upper support 1 near the first opening, the connecting thread passes through a mesh woven in the middle of the upper support 1, and then the lower end of the connecting thread is fixedly connected to a position of the top of the lower support 2 near the third opening. In such a further preferred mode, the upper support can be prevented from turning upside down to affect the fixation when the gastrointestinal stent is subjected to the upward and downward pulling forces. Moreover, the upper support contacts and supports the outside of the pyloric orifice of the stomach with an elastic surface, which can reduce or avoid damage of tissue in the digestive tract.

The gastric diverter comprises a delivery device and a built-in cannula. The delivery device consists of a handle and a delivery catheter, and the built-in cannula consists of a gastrointestinal stent and a membrane tube. The built-in cannula is introduced into a human body by means of the delivery device and is left in the duodenum. In the present disclosure, the gastrointestinal stent consists of an upper support 1 and a lower support 2 connected by a connecting thread 3 therebetween. The upper support 1 and the lower support 2 may each be woven from an elastic wire material or cut from a tubular material. The material may be a medical implantable material, such as one or more materials selected from nickel-titanium alloy, Type 316 stainless steel, polyurethane, aluminum-magnesium alloy, etc.

The stent is woven or cut into a mesh structure. The mesh opening may be in a variety of structures including a diamond shape and a hexagonal shape. The stent can be freely stretched and compressed in the transverse and longitudinal directions and can spontaneously restore to a predetermined shape and size.

The upper support 1 may be fixed at the pyloric orifice, has an opening at the lower end with a diameter larger than the maximum diameter of the opened pyloric orifice, and is in a shape including but not limited to the various shapes shown in FIGS. 3, 5, 7, 9, 10, and 11, provided that the upper support can be fixed outside the pyloric orifice and will not fall into the pyloric orifice without affecting the normal functions of the stomach and the pylorus, and without damaging the wall of the digestive tract. Different supports may be selected clinically according to actual requirements.

Preferably, the lower opening of the upper support 1 has a diameter greater than the diameter of the pyloric orifice, and preferably has a diameter of 20 to 50 mm. The upper opening preferably has a diameter of 20 to 30 mm. The upper support 1 preferably has a height of 5 to 15 mm.

The main function of the lower support 2 is to be connected to the membrane tube and to keep the upper end of the membrane tube in an open state after the bulb is opened, thereby ensuring that chyme can enter the interior of the membrane tube and be isolated from the wall of the digestive tract. The shape of the lower support 2 is designed mainly to conform to the size of the duodenal bulb of a patient and be slightly larger than the diameter of the bulb.

Preferably, the lower opening of the lower support 2 has a diameter larger than the diameter of the pyloric orifice, and preferably has a diameter of 20 to 30 mm. The upper opening preferably has a diameter of 20 to 30 mm, which is slightly larger than the diameter of the duodenal bulb of a human body. The lower support 2 preferably has a height of 5 to 15 mm.

The function of the connecting thread is to connect the upper support 1 and the lower support 2. One, two, three, or more connecting threads may be provided as depicted in FIGS. 3 to 8. The main function thereof is to connect the upper support 1 and the lower support 2. The lower support may be pulled and held by the upper support 1 via the connecting thread 3 when the lower support 2 is moving downward with the membrane tube 7, and the lower support 2 may be pulled by the connecting thread 3 when the upper support 1 is floating upward.

The connecting thread 3 may be made of a material that meets the requirements of implantation in a human body. Preferably, it may be made of one or more materials of nickel-titanium alloy, Type 316 stainless steel, polyurethane, silicone, aluminum-magnesium alloy, etc.

The outer layer of the connecting thread 3 is covered with a biocompatible soft material, in order to protect the pyloric orifice from being cut or injured by the connecting thread 3. Preferably, the covering material may be one or more materials of silicone, polyurethane, polyethylene, etc.

Both the upper support 1 and the lower support 2 are covered with protective membranes 5, in order to prevent hyperplasia and reduce damage to tissue caused by friction with the supports. The protective membrane must be made of a material that meets the requirements of implantation in a human body. Preferably, the covering membrane may be made of one or more materials of silicone, polyurethane, polyethylene, etc.

There is a certain distance between the upper support 1 and the lower support 2. Preferably, there is a distance of 20 to 60 mm between the lower end of the upper support 1 and the upper end of the lower support 2. An appropriate dimension is preferably selected depending on different anatomical structures of human bodies, based on the principle that it should be greater than the height of the pyloric ring and the lower end of the lower support 2 should be kept away from the duodenal papilla 104.

The upper support 1 and the lower support 2 are each provided with a developing ring 6, which can be clearly positioned under X-rays. The developing ring may be made of a heavy metal material that is harmless to the human body, such as platinum, gold, tantalum, or the like.

The upper ends of the upper support 1 and the lower support 2 are provided with a retrieving thread 8 and a retrieving thread 9, respectively. The retrieving threads 8 and 9 are sewn to the outermost circles of the upper support 1 and the lower support 2, respectively, so that the stent can be removed and retrieved from the human body by a specially-made retrieval device or grasping forceps. When the retrieving threads are tightened, the upper support 1 and the lower support 2 are retracted separately into a transparent cap of an endoscope or into a particular retrieval device, and are removed from the digestive tract of the human body along with the endoscope. The retrieving threads 8 and 9 may be made of biocompatible materials such as PE, nylon, polyester, etc.

A method for releasing a gastric diverter includes the gastric diverter as described above and the steps of:
1) disposing the membrane tube and the gastrointestinal stent in the folded state in the storage tube shell 13, and closing the distal opening of the storage tube shell 13 by the release body;
2) delivering the release body at the distal end of the storage tube shell 13 into the duodenum under the guidance of a guide wire, and then pushing the release body and the membrane tube out of the storage tube shell;
3) withdrawing the storage tube shell until the marking line reaches the pyloric orifice, pushing the lower support out of the storage tube shell to leave the lower support in the duodenal bulb;
4) further withdrawing the storage tube shell, pushing the upper support out of the storage tube shell to leave the upper support outside the pyloric orifice to complete the release.

Before use, the membrane tube and the gastrointestinal stent are compressed and stored in the storage tube shell 13, and the distal end is closed by the shell 11 and the core 12 of the release body. In use, the distal release body is introduced into the duodenum of a human body under the guidance of the guide wire. After the release body is unlocked, the middle tube 17 is unlocked, and the middle handle 22 is pushed to complete the first stage of delivering, where the release body and the membrane tube 7 are pushed out of the storage tube shell 13. Then, the storage tube shell 13 is withdrawn until the marking line 25 reaches the pyloric orifice, the lower support 2 is pushed out of the storage tube shell 13 to complete the second stage of delivering, and the lower support 2 is left in the duodenal bulb 103. Then, the upper support 1 is pushed out of the storage tube shell 13, and the upper support 1 is left at the pyloric orifice 102 to complete the release. Specifically, during operation of the handle, the limit ball head 23 is firstly rotated from position "0" to position "1" to unlock the middle tube 17, and the middle handle 22 is slowly pushed until it cannot be pushed any longer due to resistance, so that the first stage of delivering is completed, where the release body shell 11 and the membrane tube 7 are pushed out of the storage tube shell 13. Then, the storage tube shell 13 is withdrawn until the marking line 25 reaches the pyloric orifice, the limit ball head 23 is rotated from position "1" to position "2" to further unlock the middle tube 17, and the middle handle 22 is slowly pushed until it cannot be pushed any longer due to resistance, so that the second stage of delivering is completed, where the lower support 2 is pushed out of the storage tube shell 13, and the lower support 2 is left in the duodenal bulb 103. The limit ball head 23 is further rotated from position "2" to position "3" to unlock the middle tube 17, and the front handle 24 is pulled backward against the middle handle 22, so that the upper support 1 is pushed out of the storage tube shell 13, and the upper support 1 is left at the pyloric orifice 102 to complete the release. The membrane tube 7 reaches the upper segment of the jejunum with the peristalsis of the intestinal tract. At this time, the release body core 12 dissolves automatically, and the release body shell 11 is automatically detached from the membrane tube 7 to complete the release process. The delivery device is withdrawn from the mouth of the human body, while the built-in cannula is left in the body to achieve the effect of isolating food.

The implantable catheter can achieve the effect of isolating food in the intestinal tract and change the physiological flow direction of food. After it is implanted for a period of time, the phenomenon of insulin resistance in the patient's body is eliminated. Moreover, in this food flowing mode, secretion of insulin in the patient's body can be facilitated, apoptosis of pancreatic islet cells is reduced and the cells are proliferated, the pancreatic islet function is restored, and metabolic diseases such as diabetes and obesity are cured. The implantable catheter has a tensile modulus of 250 MP or more and an elongation greater than 230%, is made of a soft material, and therefore can significantly reduce the phenomena such as nausea, vomiting, and abdominal pain after it is implanted in the body.

The implantable catheter according to the present disclosure can be implanted in the digestive tract for the treatment of endocrine diseases such as diabetes, pancreatic islet dysfunction, and obesity, or diseases of the lower digestive tract such as inflammation. Compared with the prior art, the implantable catheter described in the present disclosure has the advantages of having a simple structure and good structural applicability, being fabricated by convenient processes with low cost at a fast production rate, having guaranteed quality, and being manufactured conveniently. Furthermore, the implantable catheter is implanted with good comfort and compliance without causing harm to human tissue.

Compared with the prior art, in the present disclosure, the upper support is fixed at the pyloric orifice, and the lower support is fixed at the duodenal bulb and is connected to the membrane tube. Both of the supports cannot move freely and can be displaced only within a small range. Specifically, the upper support will not enter the inside of the pylorus, the lower support will not enter the outside of the pylorus, and there is a connecting thread therebetween, so that the displacement range will not exceed the range of the connecting thread. The connection between the upper and lower supports has a height of 1 to 8 cm, which varies depending on different human body structures. As a result, the upper support is located outside the pylorus, the lower support is located in the duodenal bulb, and the lowermost end of the lower support does not reach the duodenal papilla and thus does not affect the normal function of the papilla. As for the main function principle of the present disclosure, a membrane tube is implanted into the duodenum and extended to the distal end of the digestive tract, so that food is isolated by the membrane tube, thereby changing the metabolic mechanism and achieving the effect of treating metabolic diseases such as obesity and diabetes. The main function of the stent is to fix the membrane tube and expand the membrane tube so that food can enter the implanted membrane tube. The extended membrane tube (sleeve) of the present disclosure has a length of 600 mm to 1600 mm and is the main functional structure. The upper support is relatively small and does not cause pressure on the stomach. The gastrointestinal stent having a structure with a smaller lower part and a larger upper part allows food to be emptied easily and not be retained. The upper support is fixed at the pyloric orifice, and the upper and lower supports cooperate with each other, so that the membrane tube is not likely to be displaced.

The present disclosure is different in both function and structure from the gastrointestinal stents disclosed in the patent documents such as Patent Publication Nos. CN102335052, CN104382671, CN204671331, and CN205359721. In the present disclosure, the upper and lower supports are in different shapes; the connecting thread is in an arcuate shape conforming to the anatomical structure of the pyloric orifice; two or more connecting threads are generally provided to allow stable connection; the product is used for the fixation at the pyloric orifice, specifically for fixation of a membrane tube for intestinal isolation, and the product is specifically used for the treatment of metabolic diseases such as diabetes and obesity. The lower support should be connected to a soft membrane tube in order to achieve the purpose of treatment.

In the description of this specification, a reference term such as "one embodiment", "some embodiments", "an example", "a specific example", or "some examples" is described to mean that a specific feature, structure, material, or characteristic described in connection with the embodiment or example is included in at least one embodiment or example of the present disclosure. In this specification, the indicative representation of the above terms does not necessarily refer to the same embodiment or example. Moreover, the described specific features, structures, materials, or characteristics can be combined in an appropriate manner in any one or more embodiments or examples.

Although the embodiments of the present disclosure have been shown and described above, it can be understood that the above embodiments are exemplary and shall not be construed as limiting the present disclosure, and the above embodiments can be changed, amended, replaced, and modified by those of ordinary skill in the art within the scope of the present disclosure without departing from the principle and purposes of the present disclosure. Any modifications, equivalent alternatives, improvements and so on made within the spirit and principle of the present disclosure are to be included in the scope of protection of the present disclosure.

What is claimed is:

1. A gastrointestinal stent of a gastric diverter, wherein the gastrointestinal stent has a pre-expansion shape and a post-expansion shape, the gastrointestinal stent comprising an upper support, a lower support, and several connecting members, wherein in the post-expansion shape, the upper support is provided with a first opening adjacent to its top and a second opening adjacent to its bottom, the first opening and the second opening allow food to pass therethrough, the lower support is disposed below the upper support, the lower support is provided with a third opening adjacent to its top and a fourth opening adjacent to its bottom, the upper support and the lower support are connected by several connecting members, the fourth opening of the lower support is connected to a membrane tube, and both of the upper support and the lower support, in the post-expansion shape, are not able to pass through an opened pyloric orifice of a stomach and the several connecting members are able to pass through the pyloric orifice of the stomach or are able to be placed through the pyloric orifice of the stomach, wherein an outer diameter of the second opening of the upper support is greater than an outer diameter of the first opening.

2. The gastrointestinal stent of the gastric diverter according to claim 1, wherein the several connecting members are at least one connecting thread.

3. The gastrointestinal stent of the gastric diverter according to claim 2, wherein the at least one connecting thread is externally covered with a membrane.

4. The gastrointestinal stent of the gastric diverter according to claim 2, wherein the several connecting members comprise a plurality of connecting threads, upper ends of the plurality of connecting threads are connected to the upper support, respectively, and lower ends of the plurality of connecting threads are connected to the lower support, respectively.

5. The gastrointestinal stent of the gastric diverter according to claim 1, wherein the several connecting members will be elastically deformed to be bent or have a reduced outer diameter in conformity with the pyloric orifice of a human body in a natural state at a position corresponding to the pyloric orifice of the stomach.

6. The gastrointestinal stent of the gastric diverter according to claim 1, wherein the upper support is in a shape of a cone, an inverted cone, a straight cylinder, or a straw hat.

7. The gastrointestinal stent of the gastric diverter according to claim 2, wherein an upper end of the at least one connecting thread is fixedly connected to a position of a top of the upper support near the first opening, and a lower end of the at least one connecting thread is fixedly connected to a position of a top of the lower support near the third opening.

8. The gastrointestinal stent of the gastric diverter according to claim 2, wherein an upper end of the at least one connecting thread is fixedly connected to a position of a top of the upper support near the first opening, the at least one connecting thread passes through a mesh woven in a middle of the upper support, and then a lower end of the at least one connecting thread is fixedly connected to a position of a top of the lower support near the third opening.

9. A gastric diverter, comprising the gastrointestinal stent according to claim 1.

10. The gastric diverter according to claim 9, comprising a storage tube shell, a release body, and a delivering component, wherein the storage tube shell is in a tubular shape, the storage tube shell is opened at both ends, the membrane tube and the gastrointestinal stent, which are in a folded state and are to be released, are disposed in the storage tube shell, the release body is disposed at a distal opening of the storage tube shell and is connected to an end of the membrane tube, the release body is made of a material capable of being digested, absorbed, or dissolved by an intestinal tract of a human body.

11. The gastric diverter according to claim 10, wherein the storage tube shell is provided with a marking line.

12. A method for releasing a gastric diverter, comprising the gastric diverter according to claim 11 and following steps:
1) disposing the membrane tube and the gastrointestinal stent in the folded state in the storage tube shell, and closing the distal opening of the storage tube shell by the release body;
2) delivering the release body at a distal end of the storage tube shell into a duodenum under a guidance of a guide wire, and then pushing the release body and the membrane tube out of the storage tube shell;
3) withdrawing the storage tube shell until the marking line reaches the pyloric orifice, pushing the lower support out of the storage tube shell to leave the lower support in a duodenal bulb; and
4) further withdrawing the storage tube shell, pushing the upper support out of the storage tube shell to leave the upper support outside the pyloric orifice, so as to complete a release.

* * * * *